(12) United States Patent
Noguchi et al.

(10) Patent No.: US 12,030,970 B2
(45) Date of Patent: Jul. 9, 2024

(54) CURABLE COMPOSITION AND STEREOLITHOGRAPHIC RESIN COMPOSITION COMPRISING SAME

(71) Applicant: KURARAY CO., LTD., Okayama (JP)

(72) Inventors: Daiki Noguchi, Niigata (JP); Takashi Fukumoto, Niigata (JP); Kenji Suzuki, Niigata (JP)

(73) Assignee: KURARAY CO., LTD., Okayama (JP)

( * ) Notice: Subject to any disclaimer, the term of this patent is extended or adjusted under 35 U.S.C. 154(b) by 177 days.

(21) Appl. No.: 17/621,282

(22) PCT Filed: Jun. 25, 2020

(86) PCT No.: PCT/JP2020/025111
§ 371 (c)(1),
(2) Date: Dec. 21, 2021

(87) PCT Pub. No.: WO2020/262564
PCT Pub. Date: Dec. 30, 2020

(65) Prior Publication Data
US 2022/0325025 A1   Oct. 13, 2022

(30) Foreign Application Priority Data

Jun. 28, 2019  (JP) .................. 2019-121873

(51) Int. Cl.
| | | |
|---|---|---|
| C08F 2/46 | (2006.01) | |
| A61K 6/887 | (2020.01) | |
| B29C 64/106 | (2017.01) | |
| C08F 2/48 | (2006.01) | |
| C08F 2/50 | (2006.01) | |
| C08F 220/30 | (2006.01) | |
| C08F 220/40 | (2006.01) | |
| C08F 220/58 | (2006.01) | |
| C08F 222/10 | (2006.01) | |
| C08G 18/24 | (2006.01) | |
| C08G 18/42 | (2006.01) | |
| C08G 18/75 | (2006.01) | |
| C08G 61/04 | (2006.01) | |
| C08K 3/36 | (2006.01) | |
| B33Y 10/00 | (2015.01) | |

(Continued)

(52) U.S. Cl.
CPC ........ *C08F 222/1065* (2020.02); *A61K 6/887* (2020.01); *B29C 64/106* (2017.08); *C08F 2/48* (2013.01); *C08F 220/301* (2020.02); *C08F 220/40* (2013.01); *C08F 220/58* (2013.01); *C08G 18/242* (2013.01); *C08G 18/4238* (2013.01); *C08G 18/755* (2013.01); *C08K 3/36* (2013.01); *B33Y 10/00* (2014.12); *B33Y 70/00* (2014.12); *B33Y 80/00* (2014.12)

(58) Field of Classification Search
CPC ........ C08F 2/48; C08F 220/30; C08F 220/58; C08F 220/40; C08F 220/306; C08F 222/1065; C08F 222/1063; C08F 290/067; C08G 18/4238; C08G 18/242; C08G 18/755; B29C 64/106; B29C 64/124; A61C 13/01; A61C 7/08; C09D 4/06; C09D 4/00; A61K 6/887; A61K 6/62; C08L 51/08; C08L 33/08; C08L 33/10; C08K 3/36; B33Y 10/00; B33Y 80/00; B33Y 70/00
USPC .................................... 522/96, 90, 1; 520/1
See application file for complete search history.

(56) References Cited

U.S. PATENT DOCUMENTS 7,211,368 B2 *  5/2007  Coats ................. B33Y 10/00
                                                   526/261
2014/0131908 A1  5/2014  Sun et al.
(Continued)

FOREIGN PATENT DOCUMENTS

| CN | 109803989 A | 5/2019 |
|---|---|---|
| JP | S56-144478 A | 11/1981 |
| JP | S60-247515 A | 12/1985 |

(Continued)

OTHER PUBLICATIONS

Mochizuki et al, JP 2012-097199 Machine Translation, May 24, 2012 (Year: 2012).*

(Continued)

*Primary Examiner* — Jessica Whiteley
(74) *Attorney, Agent, or Firm* — GREENBLUM & BERNSTEIN P.L.C.

(57) ABSTRACT

A curable composition contains 79.0 to 99.0% by mass of a polymerizable monomer (a), 0.1 to 10.0% by mass of a photopolymerization initiator (b), and 0.01 to 20.0% by mass of a compound represented by the following general formula (I) as a polyfunctional polymerizable compound (c):

$$R^1\diagdown\!\!\!\!\diagup\!\!\overset{R^2}{\diagup}\!\!\diagdown\!\!\!\!(\quad)_n\!\!\diagdown\!\!O\!\diagup\!\!R^3 \quad (I)$$

wherein $R^1$ and $R^2$ each independently represent at least one kind selected from the group consisting of a hydrogen atom, an alkyl group having 1 to 6 carbon atoms, an alkenyl group having 2 to 6 carbon atoms, an aryl group, and an aralkyl group; $R^3$ represents at least one kind of a polymerizable functional group selected from the group consisting of a (meth)acryloyl group, a 4-vinylphenyl group, and an alkenyl group having 2 to 5 carbon atoms; and n represents an arbitrary integer of 0 to 5.

18 Claims, No Drawings

(51) Int. Cl.
  *B33Y 70/00* (2020.01)
  *B33Y 80/00* (2015.01)

(56) References Cited

U.S. PATENT DOCUMENTS

2019/0254936 A1    8/2019  Suzuki et al.
2021/0246244 A1*   8/2021  Noguchi ........... C08F 220/1805

FOREIGN PATENT DOCUMENTS

| JP | H08-157534 A |   | 6/1996 |
| JP | 2012-97199 A |   | 5/2012 |
| JP | 2012097199   | * | 5/2012 |
| JP | 2015-10168 A |   | 1/2015 |

OTHER PUBLICATIONS

EESR issued in EP Patent Application No. 20830891.6, dated May 17, 2023.
ISR for PCT/JP2020/025111, dated Aug. 25, 2020.
Written Opinion for PCT/JP2020/025111, dated Aug. 25, 2020 (w/ translation).

* cited by examiner

CURABLE COMPOSITION AND STEREOLITHOGRAPHIC RESIN COMPOSITION COMPRISING SAME

TECHNICAL FIELD

The present invention relates to a curable composition and a resin composition for stereolithography prepared therefrom. More specifically, the present invention relates to a resin composition for stereolithography that is readily modeled with low viscosity in modeling by stereolithography, and is capable of providing a stereoscopic modeled article excellent in toughness and water resistance. A stereoscopic modeled article obtained by the present invention is favorable particularly for a dental mouthpiece and a denture base material.

BACKGROUND ART

PTL 1 describes a method of providing a stereoscopic modeled article by repeating an operation including supplying a required amount of controlled optical energy to a liquid photocurable resin for curing into a thin layer, further supplying a liquid photocurable resin thereon, and then irradiating with light under control for curing and laminating into a thin layer form, i.e., a so-called an optical stereoscopic modeling method. PTL 2 describes a basic practical method thereof, and since then, many proposals relating to the optical stereoscopic modeling technique have been made.

As a representative method for optically producing a stereoscopic modeled article, a method referred to as vat stereolithography has been employed, which repeats a lamination operation including selectively irradiating a liquid surface of a liquid photocurable resin composition placed in a vat with an ultraviolet ray laser controlled with a computer to provide a prescribed pattern, so as to cure in a prescribed thickness, resulting in a cured layer, then supplying the liquid photocurable resin composition in an amount corresponding to one layer to the cured layer, and similarly irradiating with ultraviolet ray laser to cure, resulting in a continuous cured layer, and thus produces a stereoscopic modeled article having the final shape. The method is receiving increasing attention in recent years since a target stereoscopic modeled article can be produced with high accuracy in a convenient manner within a relatively short period of time even though the modeled article has a considerably complicated shape.

A stereoscopic modeled article obtained by the stereolithography is now being expanded from a simple conceptual model to a trial model, a prototype model, and the like, and associated thereto, the stereoscopic modeled article is increasingly demanded to have excellent modeling accuracy. Furthermore, the stereoscopic modeled article is also demanded to have excellent characteristics corresponding to the application thereof, in addition to the aforementioned characteristics. In the field of dental materials, in particular, a dental mouthpiece and a denture base material are different in shape for each patient and have complicated shapes, and therefore the application of stereolithography thereto is being expected.

The dental mouthpieces include a dental aligner mounted on a row of teeth for orthodontics, a dental splint mounted for jaw position correction, a mouthpiece mounted on a row of teeth during sleeping at night for treating the sleep apnea syndrome, a mouthpiece mounted on a row of teeth for suppressing abrasion of teeth due to clenching, and a mouthpiece mounted in an oral cavity for reducing external injuries occurring due to an external force applied to teeth or jawbone during sports activities and for protecting the stomatognathic system and the brain. The use of the dental mouthpieces is rapidly spread in orthodontics in recent years due to the good esthetics and the casual detachability thereof. The sleep apnea syndrome is receiving attention in the medical field, and the use of the dental mouthpieces is rapidly spread as a therapeutic device therefor.

A denture base material is used in the gingiva portion of a denture mounted due to loss of teeth. Due to the increase of the elderly population in recent years, the demand of dentures is being rapidly increased.

The dental mouthpiece and the denture base material are commonly demanded to have toughness and water resistance. With poor toughness, the wearing feeling may be deteriorated, and an impact of an external force or occlusion is applied directly to the jawbone. Furthermore, there may be a problem that the frequent remaking is required due to the fragility thereof. Moreover, there may be a problem that the deterioration of the water resistance may decrease the mechanical characteristics, resulting in loss of the orthodontic force or the shock absorbability, and lack of practicality due to fragility.

In the production of the dental mouthpiece, the denture base material, and the sleep apnea syndrome treatment device, it is generally necessary to take an impression of the oral cavity, but the problems have been noted that the discomfort thereof becomes a burden on patients, and an expert technical operation is required therefor. According to the development of digital technologies in recent years, there is an attempt to take the impression by optically scanning the oral cavity, and in modeling, there is an attempt to apply the optical stereoscopic modeling. A photocurable resin composition is used for modeling, but a resin composition exhibiting flexibility and water resistance generally tends to use a monomer having low polarity resulting in low curing capability, resulting in a tendency that the cured article has a deteriorated mechanical strength, and particularly in optical stereoscopic modeling, since the light irradiation time is extremely short, and the resin composition is exposed to oxygen in modeling every layer, the curing thereof tends to be insufficient, which has made it difficult to achieve all the mechanical strength, the toughness, and the water resistance simultaneously. Furthermore, while the resin composition necessarily has viscosity that enables modeling, there is a problem that the curing capability is deteriorated in the case where a monomer having a small molecular weight is used for decreasing the viscosity, but a monomer exhibiting the mechanical strength frequently has high viscosity deteriorating the modeling capability.

Under the circumstances, as a technique enabling optical stereoscopic modeling with the excellent modeling accuracy, and the excellent mechanical strength and swelling resistance of the cured article, for example, PTL 3 proposes a resin composition for optical stereoscopic modeling containing as essential components an α,β-unsaturated double bond group-containing compound having both a (meth)acryloyl group and an alkenyl group.

CITATION LIST

Patent Literatures

PTL 1: JP 56-144478 A
PTL 2: JP 60-247515 A
PTL 3: JP 2015-10168 A

SUMMARY OF INVENTION

Technical Problem

PTL 3 does not specifically describe about the enhancement of the toughness and the water resistance of the photocurable resin composition described therein.

An object of the present invention is to provide a curable composition that is readily modeled with low viscosity and excellent curing capability in modeling by stereolithography, and provides a cured article excellent in toughness and water resistance, and a resin composition for stereolithography prepared therefrom. Another object thereof is to provide a resin composition for stereolithography that is favorable particularly for a dental mouthpiece and a denture base material.

Solution to Problem

The present invention relates to the following items.

[1] A curable composition containing 79.0 to 99.0% by mass of a polymerizable monomer (a), 0.1 to 10.0% by mass of a photopolymerization initiator (b), and 0.01 to 20.0% by mass of a compound represented by the following general formula (I) as a polyfunctional polymerizable compound (c):

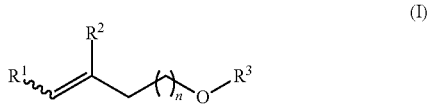

(I)

wherein $R^1$ and $R^2$ each independently represent at least one kind selected from the group consisting of a hydrogen atom, an alkyl group having 1 to 6 carbon atoms, an alkenyl group having 2 to 6 carbon atoms, an aryl group, and an aralkyl group; $R^3$ represents at least one kind of a polymerizable functional group selected from the group consisting of a (meth)acryloyl group, a 4-vinylphenyl group, and an alkenyl group having 2 to 5 carbon atoms; and n represents an arbitrary integer of 0 to 5.

[2] A resin composition for stereolithography containing the curable composition according to the item W.

[3] The resin composition for stereolithography according to the item [2], wherein in the general formula (I), $R^3$ represents a hydrogen atom.

[4] The resin composition for stereolithography according to the item [2] or [3], wherein in the general formula (I), RP represents a (meth)acryloyl group.

[5] The resin composition for stereolithography according to any one of the items [2] to [4], wherein the polyfunctional polymerizable compound (c) is represented by the following general formula (II);

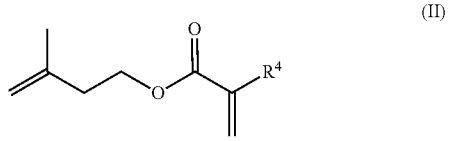

(II)

wherein $R^4$ represents a hydrogen atom or a methyl group.

[6] The resin composition for stereolithography according to any one of the items [2] to [5], wherein the polymerizable monomer (a) contains a polymerizable monomer (a)-1 containing plural polymerizable groups.

[7] The resin composition for stereolithography according to the item [6], wherein the polymerizable monomer (a)-1 contains a urethanated (meth)acrylic compound (a)-1α.

[8] The resin composition for stereolithography according to any one of the items [2] to [7], wherein the polymerizable monomer (a) contains a monofunctional polymerizable monomer (a)-2.

[9] The resin composition for stereolithography according to the item [8], wherein the monofunctional polymerizable monomer (a)-2 contains a ring structure.

[10] The resin composition for stereolithography according to any one of the items [2] to [9], wherein the resin composition further contains inorganic particles (d).

[11] A stereolithography resin cured article containing a cured article of the resin composition for stereolithography according to any one of the items [2] to [10].

[12] A dental material containing a cured article of the resin composition for stereolithography according to any one of the items [2] to [10].

[13] A dental mouthpiece containing a cured article of the resin composition for stereolithography according to any one of the items [2] to [10].

[14] A denture base material containing a cured article of the resin composition for stereolithography according to any one of the items [2] to [10].

[15] A medical material containing a cured article of the resin composition for stereolithography according to any one of the items [2] to [10].

[16] A sleep apnea syndrome treatment device containing a cured article of the resin composition for stereolithography according to any one of the items [2] to [10].

[17] A method for producing a stereoscopic modeled article by an optical stereoscopic modeling method, including using the resin composition for stereolithography according to any one of the items [2] to [10].

Advantageous Effects of Invention

The curable composition and the resin composition for stereolithography prepared therefrom according to the present invention are readily modeled with low viscosity and excellent curing capability in modeling by stereolithography, and provide a cured article excellent in toughness and water resistance, and therefore can be favorably applied to various dental materials, particularly to a dental mouthpiece, a denture base material, and the like.

DESCRIPTION OF EMBODIMENTS

The curable composition of the present invention contains a polymerizable monomer (a), a photopolymerization initiator (b), a polyfunctional compound (c), and depending on necessity inorganic particles (d). The resin composition for a stereolithography containing the curable composition is readily modeled with low viscosity and excellent curing capability in modeling by stereolithography, and provides a cured article excellent in toughness and water resistance.

In the description herein, the upper limit values and the lower limit values of the numerical ranges (for example, the contents of the components, the values calculated from the components, and the property values) may be arbitrarily combined.

[Polymerizable Monomer (a)]

The polymerizable monomer (a) used in the present invention is preferably a radical polymerizable monomer.

Specific examples of the radical polymerizable monomer as the polymerizable monomer (a) include a (meth)acrylate based polymerizable monomer; a (meth)acrylamide based polymerizable monomer; ester compounds of α-cyanoacrylic acid, (meth)acrylic acid, α-haloacrylic acid, crotonic acid, cinnamic acid, sorbic acid, maleic acid, itaconic acid, and the like; a vinyl ester compound; a vinyl ether compound; a mono-N-vinyl derivative; and a styrene derivative. Among these, a (meth)acrylate based polymerizable monomer and a (meth)acrylamide based polymerizable monomer are preferred from the standpoint of the curing capability. These compounds may be used alone or as a combination of two or more kinds thereof.

Examples of the polymerizable monomer (a) in the present invention include a polymerizable monomer (a)-1 containing plural polymerizable groups and a monofunctional polymerizable monomer (a)-2. The polymerizable monomer (a)-1 containing plural polymerizable groups is preferably used from the standpoint of the curing capability, the monofunctional polymerizable monomer (a)-2 is preferably used from the standpoint of the easiness in achieving low viscosity, and both the polymerizable monomer (a)-1 containing plural polymerizable groups and the monofunctional polymerizable monomer (a)-2 are preferably used from the standpoint of the toughness.

The polymerizable monomer (a)-1 containing plural polymerizable groups is preferably bifunctional from the standpoint that the cured article is excellent in toughness.

Examples of the polymerizable monomer containing plural polymerizable groups include a polymerizable monomer containing a urethane bond and plural polymerizable groups (i.e., a urethanated (meth)acrylic compound (a)-1α) and a polymerizable monomer containing plural polymerizable groups containing no urethane bond, and the urethanated (meth)acrylic compound (a)-1α is preferably contained from the standpoint of the toughness.

The urethanated (meth)acrylic compound (a)-1α can be readily synthesized, for example, by subjecting a polyol having a polymer skeleton described later, a compound having an isocyanate group (—NCO), and a (meth)acrylate compound having a hydroxy group (—OH) to addition reaction. The urethanated (meth)acrylic compound (a)-1α can also be readily synthesized, for example, by subjecting a (meth)acrylate compound having a hydroxy group and a lactone or an alkylene oxide to ring-opening addition reaction, and then subjecting the resulting compound having a hydroxy group at one end thereof and a compound having an isocyanate group to addition reaction.

The urethanated (meth)acrylic compound (a)-1α is preferably a (meth)acrylate having in one molecule thereof at least one structure selected from the group consisting of a polyester, a polycarbonate, a polyurethane, a polyether, a poly(conjugated diene), and a hydrogenated poly(conjugated diene), and a urethane bond. In the structures, examples of the polyester include a polymer of phthalic acid and an alkylenediol having 2 to 12 carbon atoms, a polymer of adipic acid and an alkylene glycol having 2 to 12 carbon atoms, a polymer of sebacic acid and an alkylene glycol having 2 to 12 carbon atoms, a polymer of maleic acid and an alkylenediol having 2 to 12 carbon atoms, a polymer of β-propiolactone, a polymer of γ-butyrolactone, a polymer of δ-valerolactone, a polymer of ε-caprolactone, and copolymers thereof. Examples of the polycarbonate include a polycarbonate derived from an aliphatic diol having 2 to 12 carbon atoms, a polycarbonate derived from bisphenol A, and a polycarbonate derived from an aliphatic diol having 2 to 12 carbon atoms and bisphenol A. Examples of the polyurethane include a polymer of an aliphatic diol having 2 to 12 carbon atoms and a diisocyanate having 1 to 12 carbon atoms. Examples of the polyether include polyethylene glycol, polypropylene glycol, polybutylene glycol, and poly(1-methylbutylene glycol). Examples of the poly (conjugated diene) and a hydrogenated poly(conjugated diene) include 1,4-polybutadiene, 1,2-polybutadiene, polyisoprene, poly(butadiene-isoprene), poly(butadiene-styrene), poly(isoprene-styrene), polyfarnesene, and hydrogenated products thereof. Among these, a structure of a polyester is preferred from the standpoint of the excellent toughness thereof.

Examples of the compound having an isocyanate group include hexamethylene diisocyanate (HDI), tolylene diisocyanate (TDI), xylylene diisocyanate (XDI), diphenylmethane diisocyanate (MDI), isophorone diisocyanate (IPDI), trimethylhexamethylene diisocyanate (TMHMDI), tricyclodecane diisocyanate (TCDDI), and adamantane diisocyanate (ADI).

Examples of the (meth)acrylate compound having a hydroxy group include a hydroxy (meth)acrylate, such as 2-hydroxyethyl (meth)acrylate, 2-hydroxypropyl (meth) acrylate, 2-hydroxybutyl (meth)acrylate, 6-hydroxyhexyl (meth)acrylate, 10-hydroxydecyl (meth)acrylate, 3-chloro-2-hydroxypropyl (meth)acrylate, 2-hydroxy-3-phenoxypropyl (meth)acrylate, glycerin mono(meth)acrylate, N-hydroxyethyl (meth)acrylamide, N,N-bis(2-hydroxyethyl) (meth)acrylamide, 2-hydroxy-3-acryloyloxypropyl (meth) acrylate, 2,2-bis(4-(3-(meth)acryloyloxy-2-hydroxypropoxy)phenyl)propane, 1,2-bis(3-(meth)acryloyloxy-2-hydroxypropoxy)ethane, pentaerythritol tri(meth)acrylate, and dipentaerythritol tri- or tetra(meth)acrylate.

In the present invention, the expression "(meth)acryloyloxy" shows the meaning encompassing both methacryloyloxy and acryloyloxy.

The addition reaction of the compound having an isocyanate group and the (meth)acrylate compound having a hydroxy group may be performed according to a known method, which is not particularly limited.

Examples of the urethanated (meth)acrylic compound (a)-1α obtained include a reaction product of an arbitrary combination of the polyol having at least one structure selected from the group consisting of a polyester, a polycarbonate, a polyurethane, a polyether, a poly(conjugated diene), and a hydrogenated poly(conjugated diene), the compound having an isocyanate group, and the (meth) acrylate compound having a hydroxy group.

The weight average molecular weight (Mw) of the urethanated (meth)acrylic compound (a)-1α is preferably 1,000 to 30,000, more preferably 1,500 to 15,000, and further preferably 2,000 to 5,000, from the standpoint of the viscosity and the strength. The weight average molecular weight (Mw) in the present invention means a weight average molecular weight in terms of polystyrene conversion measured by gel permeation chromatography (GPC).

The content of the urethanated (meth)acrylic compound (a)-1α in the present invention is preferably 5.0 to 90.0% by mass, and is more preferably 10.0 to 80.0% by mass, and further preferably 15.0 to 70.0% by mass, from the standpoint of the excellent modeling capability, and the excellent toughness and water resistance of the cured article, all based on the total amount of the polymerizable monomer (a) and the polyfunctional polymerizable compound (c).

Examples of the polymerizable monomer containing plural polymerizable groups containing no urethane bond include 2,2-bis((meth)acryloyloxyphenyl)propane, 2,2-bis (4-(3-acryloyloxy)-2-hydroxypropoxyphenyl)propane, 2,2- bis(4-(3-methacryloyloxy)-2-hydroxypropoxyphenyl)propane (trivial name: Bis-GMA), 2,2-bis(4-(meth)acryloyloxyethoxyphenyl)propane, 2,2-bis(4-(meth)acyrloyloxypolyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, 2,2-bis(4-(meth)acryloyloxyisopropoxyphenyl)propane, 1,4-bis(2-(meth)acryloyloxyethyl) pyromellitate, glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, polyethylene glycol di(meth)acrylate, 1,3-butanediol di(meth)acrylate, 1,4-butanediol di(meth)acrylate, 1,6-hexanediol di(meth)acrylate, 2-ethyl-1,6-hexanediol di(meth)acrylate, 1,9-nonanediol di(meth)acrylate, 1,10-decanediol di(meth)acrylate, and 1,2-bis(3-methacryloyloxy-2-hydroxypropoxy)ethane. Among these, 2,2-bis(4-(3-methacryloyloxy)-2-hydroxypropoxyphenyl)propane and 2,2-bis(4-methacryloyloxypolyethoxyphenyl)propane are preferred from the standpoint of the toughness and the curing capability.

Examples of the trifunctional or higher polymerizable monomer include trimethylolpropane tri(meth)acrylate, trimethylolethane tri(meth)acrylate, trimethylolmethane tri (meth)acrylate, pentaerythritol tri(meth)acrylate, pentaerythritol tetra(meth)acrylate, dipentaerythritol penta(meth)acrylate, and 1,7-diacryloyloxy-2,2,6,6-tetra(meth)acryloyloxymethyl-4-oxyheptane.

The content of the polymerizable monomer containing plural polymerizable groups containing no urethane bond in the present invention is preferably 0 to 40.0% by mass, and is more preferably 1.0 to 30.0% by mass, and further preferably 2.5 to 20.0% by mass, from the standpoint of the excellent toughness and water resistance of the cured article, all based on the total amount of the polymerizable monomer (a) and the polyfunctional polymerizable compound (c).

Examples of the monofunctional polymerizable monomer (a)-2 include a polymerizable monomer containing a ring structure and a polymerizable monomer containing no ring structure, and a ring structure is preferably contained therein from the standpoint of the curing capability and the toughness.

Examples of the ring structure are not particularly limited, as far as the effects of the present invention are exhibited, and include a cycloalkane series, such as a biphenyl ring, a phenoxybenzene ring, a bicyclo[1.1.1]pentane ring, a (1r,4r)-bicyclo[2.1.1]hexane ring, (1s,4s)-bicyclo[2.2.1]heptane ring (trivial name: norbornane ring), a bicyclo[2.2.2]octane ring, a (1r,5r)-bicyclo[3.1.1]heptane ring, a (1R,5S)-bicyclo[3.2.1]octane ring, a (1R,5S)-bicyclo[3.3.1]nonane ring, a bicyclo[3.3.2]decane ring, a bicyclo[3.3.3]undecane ring, a (1r,6r)-bicyclo[4.2.2]decane ring, (1r,6r)-bicyclo[4.3.2]undecane ring, a (1r,6r)-bicyclo[4.3.3]dodecane ring, a (1R,6S)-bicyclo[4.2.1]nonane ring, a (1R,6S)-bicyclo[4.3.1]decane ring, a (3aR,4R,7S,7aS)-octahydro-1H-4,7-methanoindene ring (trivial name: dicyclopentanyl ring), a (1R,4S,4as,5R,8S)-decahydro-1,4:5,8-dimethanonapthalene ring (trivial name: tetracyclododecanyl ring), a tricyclo[1.1.0.0$^{2,4}$]butane ring, a pentacyclo[2.1.0.0$^{1,3}$.0$^{2,4}$.0$^{2,5}$]pentane ring, a tetracyclo[2.1.0$^{1,3}$.0$^{2,5}$]pentane ring, a heptacyclo[2.2.0.0$^{1,3}$.0$^{2,5}$.0$^{2,6}$.0$^{3,5}$.0$^{4,6}$]hexane ring, an adamantane ring, a (1s,4s)-bicyclo[2.2.1]hept-2-ene ring (trivial name: norbornene ring), a (3aR,4R,7R,7aR)-hexahydro-1H-4,7-methanoindene ring (trivial name: dicyclopentenyl ring), a (1R,4S,5S,8R,8aR)-1,2,3,4,4a,5,8,8α-octahydro-1,4:5,8-methanonaphthalene ring (trivial name: tricyclododecanyl ring), a [1,1]paracyclophane ring, a [2,2]paracyclophane ring, a [2,2]metacyclophane ring, a [2,2,2,2](1,2,4,5)cyclophane ring, a 9,10-dihydro-9,10-[1,2]benzenoanthracene ring, a cyclopentane ring, a cyclohexane ring, a cycloheptane ring, a cyclooctane ring, a cyclononane ring, a cyclodecane ring, a cyclododecane ring, a cyclohexadecane ring, a (1s,3s)-bicyclo[1.1.0]butane ring, a (1R,4S)-bicyclo[2.1.0]pentane ring, a (1R,5s)-bicyclo[3.1.0]hexane ring, a (1R,5s)-bicyclo[3.2.0]heptane ring, a (3as,6as)-octahydropentalene ring, a (1R,6S)-bicyclo[4.1.0]heptane ring, a (1R,6S)-bicyclo[4.2.0]octanone ring, a (3aR,7aS)-octahydro-1H-indene ring, a (4as,8as)-decahydronaphthalene ring, a (4ar,8ar)-decahydronaphthalene ring, a decahydronaphthalene ring, and a tetradecahydronaphthalene ring; a cycloalkene series, such as a cyclopentene ring, a cyclohexene ring, a cycloheptene ring, a cyclooctene ring, a cyclobutadiene ring, a cyclopentadiene ring, a cyclohexadiene ring, a cycloheptadiene ring, a cyclooctadiene ring, an octahydronaphthalene ring, and a dodecahydroanthracene; a [4n+2]annulene series having 3 or more ring carbon atoms, such as a benzene ring, a cyclooctatetraene ring, a cyclotetradecaheptaene ring, and a cyclooctadecanonaene ring; an aromatic condensed bicyclic series, such as a naphthalene ring, a pentalene ring, an indene ring, an indane ring, a tetralin ring, and an azulene ring; a hydrocarbon ring, for example, a carbon-condensed tricyclic series, such as an as-indacene ring, an s-indacene ring, a biphenylene ring, an acenaphthylene ring, an acenaphthene ring, a fluorene ring, a phenalene ring, a perinaphthene ring, a phenanthrene ring, and an anthracene ring; a heterocyclic series containing only a nitrogen atom, represented by a saturated monocyclic series containing one nitrogen atom, such as an ethyleneimine ring, an azetidine ring, a pyrrolidine ring, a piperidine ring, an azepane ring, a quinuclidine ring, and a tropane ring; a saturated monocyclic series containing two or more nitrogen atoms, such as a piperazine ring and a methenamine ring; an unsaturated monocyclic series containing one nitrogen atom, such as an azirine ring, an azete ring, a pyrrole ring, a pyridine ring, a quinuclidine ring, and an azepine ring; unsaturated monocyclic series containing two or more nitrogen atoms, such as an imidazole ring, an indazole ring, an imidazoline ring, a pyrazole ring, a pyrazine ring, a pyrimidine ring, a pyridazine ring, a triazole ring, a triazine ring, and a tetrazole ring; an unsaturated polycyclic series containing one nitrogen atom, such as an indole ring, an isoindole ring, a quinoline ring, an isoquinoline ring, a carbazole ring, and an acridine ring; and an unsaturated polycyclic series containing two or more nitrogen atoms, such as a benzimidazole ring, a quinoxaline ring, a quinazoline ring, a phthalazine ring, a cinnoline ring, a pteridine ring, a naphthyridine ring, a purine ring, a benzotriazole ring, a phenazine ring, a benzodiazepine ring, a benzo-o-cinnoline ring, a porphyrin ring, a chlorin ring, and a choline ring; and a heterocyclic series containing both a nitrogen atom and an oxygen atom, such as a morpholine ring, a lactam ring, an isatin ring, a primidone ring, an oxazine ring, an oxazole ring, an isoxazole ring, a benzoxazine ring, a phenoxazine ring, a benzophenoxazine ring, a phenazone ring, a hydantoin ring, and a phthalocyanine ring, and among these, a biphenyl ring, a phenoxybenzene ring, a pyrrolidine ring, a piperidine ring, and morpholine ring are preferred from the standpoint of the modeling capability.

Examples of the polymerizable monomer (a)-2 containing a ring structure include a cyclic (meth)acrylate ester compound, such as o-phenylphenol (meth)acrylate, m-phenylphenol (meth)acrylate, p-phenylphenol (meth)acrylate, methoxylated o-phenylphenol (meth)acrylate, methoxylated m-phenylphenol (meth)acrylate, methoxylated p-phenylphenol (meth)acrylate, ethoxylated o-phenylphenol (meth)acrylate, ethoxylated m-phenylphenol (meth)acrylate, ethoxylated p-phenylphenol (meth)acrylate, propoxylated o-phenylphenol (meth)acrylate, propoxylated m-phenylphenol (meth)acrylate, propoxylated p-phenylphenol (meth)acrylate, butoxylated o-phenylphenol (meth)acrylate, butoxylated m-phenylphenol (meth)acrylate, butoxylated p-phenylphenol (meth)acrylate, o-phenoxybenzyl (meth)acrylate, m-phenoxybenzyl (meth)acrylate, p-phenoxybenzyl (meth)acrylate, 2-(o-phenoxyphenyl)ethyl (meth)acrylate, 2-(m-phenoxyphenyl)ethyl (meth)acrylate, 2-(p-phenoxyphenyl)ethyl (meth)acrylate, 3-(o-phenoxyphenyl)propyl (meth)acrylate, 3-(m-phenoxyphenyl)propyl (meth)acrylate, 3-(p-phenoxyphenyl)propyl (meth)acrylate, 4-(o-phenoxyphenyl)butyl (meth)acrylate, 4-(m-phenoxyphenyl)butyl (meth)acrylate, 4-(p-phenoxyphenyl)butyl (meth)acrylate, 5-(o-phenoxyphenyl)pentyl (meth)acrylate, 5-(m-phenoxyphenyl)pentyl (meth)acrylate, 5-(p-phenoxyphenyl)pentyl (meth)acrylate, 6-(o-phenoxyphenyl) hexyl (meth)acrylate, 6-(m-phenoxyphenyl)hexyl (meth)acrylate, 6-(p-phenoxyphenyl)hexyl (meth)acrylate, 2-(1-adamantyl) propyl (meth)acrylate, 2-methyladamantyl-2-yl (meth)acrylate, 2-ethyladamantyl-2-yl (meth)acrylate, 2-n-propyladamantyl-2-yl (meth)acrylate, 2-isopropyladamantyl-2-yl (meth)acrylate, 1-(adamantan-1-yl)-1-methylethyl (meth)acrylate, 1-(adamantan-1-yl)-1-ethylethyl (meth)acrylate, 1-(adamantan-1-yl)-1-methylpropyl (meth)acrylate, and 1-(adamantan-1-yl)-1-ethylpropyl (meth)acrylate; a (meth)acrylate ester compound containing a hydrocarbon ring, such as 4-biphenylyl (meth)acrylate, 2-oxo-1,2-diphenylethyl (meth)acrylate, 1-naphtyl (meth)acrylate, 2-naphtyl (meth)acrylate, 1-naphtylmethyl (meth)acrylate, 1-anthryl (meth)acrylate, 2-anthryl (meth)acrylate, 9-anthryl (meth)acrylate, 9-anthrylmethyl (meth)acrylate, o-2-propenylphenyl (meth)acrylate, trityl (meth)acrylate, cyclohexyl (meth)acrylate, isobornyl (meth)acrylate, benzyl (meth)acrylate, and phenyl (meth)acrylate; a cyclic (meth)acrylate ester compound containing a nitrogen atom, such as pentamethylpiperidinyl (meth)acrylate, tetramethylpiperidinyl (meth)acrylate, and 4-(pyrimidin-2-yl)piperadin-1-yl (meth)acrylate; a cyclic (meth)acrylamide compound, such as N-(meth)acryloylpyrrolidine, N-(meth)acryloylpiperidine, N-(meth)acryloyl-2-methylpiperidine, and N-(meth)acryloyl-2,2,6,6-tetramethylpiperidine; a polycyclic (meth)acrylate ester compound containing a nitrogen atom, such as 2-(2'-hydroxy-5'-(meth)acryloyloxyethylphenyl)-2H-benzotriazole, 2-(2'-hydroxy-5'-(meth)acryloyloxyethylphenyl)-5-chloro-2H-benzotriazole, 2-(2'-hydroxy-5'-(meth)acryloyloxypropylphenyl)-2H-benzotriazole, 2-(2'-hydroxy-5'-(meth)acryloyloxypropylphenyl)-5-chloro-2H-benzotriazole, 2-(2'-hydroxy-3'-tert-butyl-5'-(meth)acryloyloxyethylphenyl)-2H-benzotriazole, and 2-(2'-hydroxy-3'-tert-butyl-5'-(meth)acryloyloxyethylphenyl)-5-chloro-2H-benzotriazole; a (meth)acrylate ester compound having a nitrogen atom-containing 6-membered ring, such as 2,4-diphenyl-6-[2-hydroxy-4-{2-(meth)acryloyloxyethoxy}]-S-triazine, 2,4-bis(2-methylphenyl)-6-[2-hydroxy-4-{2-(meth)acryloyloxyethoxy}]-S-triazine, 2,4-bis(2-methoxyphenyl)-6-[2-hydroxy-4-{2-(meth)acryloyloxyethoxy}]-S-triazine, 2,4-bis(2-ethylphenyl)-6-[2-hydroxy-4-{2-(meth)acryloyloxyethoxy}]-S-triazine, 2,4-bis(2-ethoxyphenyl)-6-[2-hydroxy-4-{2-(meth)acryloyloxyethoxy}]-S-triazine, 2,4-bis(2,4-dimethylphenyl)-6-[2-hydroxy-4-{2-(meth)acryloyloxyethoxy}]-S-triazine, 2,4-bis(2,4-diethoxyphenyl)-6-[2-hydroxy-4-{2-(meth)acryloyloxyethoxy}]-S-triazine, and 2,4-bis(2,4-diethylphenyl)-6-[2-hydroxy-4-{2-(meth)acryloyloxyethoxy}]-S-triazine; a (meth)acylate ester compound having a ring structure containing an oxygen atom in addition to a nitrogen atom, such as imide (meth)acrylate, 2-(4-oxazolin-3-yl)ethyl (meth)acrylate, ethoxylated isocyanuric acid tri(meth)acrylate, and ε-caprolactone-modified tris(2-acryloyloxyethyl) isocyanurate; and a cyclic acrylamide compound, such as 4-acryloylmorpholine, and among these, from the standpoint of the achievement of the excellent toughness and water resistance of the cured article of the resin composition for stereolithography of the present invention, o-phenoxybenzyl acrylate, m-phenoxybenzyl acrylate, p-phenoxybenzyl acrylate, 2-(o-phenoxyphenyl)ethyl acrylate, 2-(m-phenoxyphenyl)ethyl acrylate, 2-(p-phenoxyphenyl)ethyl acrylate, N-(meth)acryloylmorpholine, pentamethylpiperidinyl (meth)acrylate, and tetramethylpiperidinyl (meth)acrylate are more preferred, o-phenoxybenzyl acrylate, m-phenoxybenzyl acrylate, 2-(o-phenoxyphenyl)ethyl acrylate, 2-(m-phenoxyphenyl)ethyl acrylate, N-(meth)acryloylmorpholine, pentamethylpiperidinyl (meth)acrylate, and tetramethylpiperidinyl (meth)acrylate are further preferred, and m-phenoxybenzyl acrylate, 2-(o-phenoxyphenyl)ethyl acrylate, N-(meth)acryloylmorpholine, and pentamethylpiperidinyl (meth)acrylate are most preferred.

The content of the monofunctional polymerizable monomer (a)-2 in the present invention is preferably 5.0 to 90.0% by mass, and is more preferably 10.0 to 80.0% by mass, further preferably 20.0 to 70.0% by mass, still further preferably 30.0 to 60.0, and particularly preferably 35.0 to 55.0, from the standpoint of the excellent modeling capability, and the excellent toughness and water resistance of the cured article, all based on the total amount of the polymerizable monomer (a) and the polyfunctional polymerizable compound (c).

Examples of the polymerizable monomer (a)-2 containing no ring structure include 2-hydroxyethyl (meth)acrylate, 2-hydroxypropyl (meth)acrylate, 3-hydroxypropyl (meth)acrylate, 4-hydroxybutyl (meth)acrylate, 6-hydroxyhexyl (meth)acrylate, 10-hydroxydecyl (meth)acrylate, propylene glycol mono(meth)acrylate, glycerol mono(meth)acrylate, erythritol mono(meth)acrylate, methyl (meth)acrylate, ethyl (meth)acrylate, propyl (meth)acrylate, isopropyl (meth)acrylate, n-butyl (meth)acrylate, sec-butyl (meth)acrylate, t-butyl (meth)acrylate, isobutyl (meth)acrylate, n-hexyl (meth)acrylate, lauryl (meth)acrylate, cetyl (meth)acrylate, stearyl (meth)acrylate, 2,3-dibromopropyl (meth)acrylate, 3-(meth)acryloyloxypropyltrimethoxysilane, 11-(meth)acryloyloxyundecyltrimethoxysilane, and (meth)acrylamide. Examples of the monofunctional (meth)acrylamide based polymerizable monomer include N,N-dimethyl (meth)acrylamide, N,N-diethyl (meth)acrylamide, N,N-di-n-propyl (meth)acrylamide, N,N-di-n-butyl (meth)acrylamide, N,N-di-n-hexyl (meth)acrylamide, N,N-di-n-octyl (meth)acrylamide, N,N-di-2-ethylhexyl (meth)acrylamide, N-hydroxyethyl (meth)acrylamide, and N,N-(dihydroxyethyl) acrylamide. These compounds may be used alone or as a combination of two or more kinds thereof. Among these, the (meth)acrylamide based polymerizable monomer is preferred, and therein N-(meth)acryloylmorpholine, N,N-dimethyl (meth)acrylamide, and N,N-diethyl (meth)acrylamide are more preferred, from the standpoint of the excellent curing capability.

The curable composition of the present invention contains the polymerizable monomer (a) in an amount of 79.0 to 99.0% by mass. In the case where the content of the polymerizable monomer (a) is less than 79.0% by mass, the modeling capability, and the toughness and the water resistance of the cured article are deteriorated. In this standpoint, the content of the polymerizable monomer (a) in the curable composition is preferably 82.0 to 97.0% by mass, more preferably 85.0 to 95.0% by mass, and further preferably 87.0 to 95.0% by mass.

[Photopolymerization Initiator (b)]

The photopolymerization initiator (b) used in the present invention may be selected from photopolymerization initiators having been used in ordinary industries, and among these, a photopolymerization initiator used in dental purpose is preferably used.

Examples of the photopolymerization initiator (b) include a (bis)acylphosphine oxide compound, a thioxanthone compound or a quaternary ammonium salt of a thioxanthone compound, a ketal compound, an α-diketone compound, a coumarin compound, an anthraquinone compound, a benzoin alkyl ether compound, and an α-aminoketone compound. These compounds may be used alone or as a combination of two or more kinds thereof.

Among these photopolymerization initiators (b), at least one kind selected from the group consisting of a (bis) acylphosphine oxide compound and a salt thereof, and an α-diketone compound is preferably used. With the use thereof, the resin composition for stereolithography that is excellent in photocuring capability in the ultraviolet region and the visible light region, and shows sufficient photocuring capability with any light source including a laser, such as an Ar laser and a He-Cd laser, and an illumination, such as a halogen lamp, a xenon lamp, a metal halide lamp, a light emitting diode (LED), a mercury lamp, and a fluorescent lamp, can be obtained.

Examples of the acylphosphine oxide compound in the (bis)acylphosphine oxide compound used as the photopolymerization initiator (b) include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyldi-(2,6-dimethylphenyl)phosphonate, 2,4,6-trimethylbenzoylphenylphosphine oxide sodium salt, 2,4,6-trimethylbenzoyldiphenylphosphine oxide potassium salt, and 2,4,6-trimethylbenzoyldiphenylphosphine oxide ammonium salt. Examples of the bisacylphosphine oxide compound include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, and bis(2,5,6-trimethylbenzoyl)-2,4,4-trimethylpentylphosphine oxide. Examples thereof also include the compounds described in JP 2000-159621 A.

Among the (bis)acylphosphine oxide compounds, 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and 2,4,6-trimethylbenzoylphenylphosphine oxide sodium salt are particularly preferred.

Examples of the α-diketone compound used as the photopolymerization initiator (b) include diacetyl, benzyl, camphorquinone, 2,3-pentadione, 2,3-octadione, 9,10-phenanthrenequinone, 4,4'-oxybenzyl, and acenaphthenequinone. Among these, camphorquinone is particularly preferred in the case where a light source in the visible light region is used.

The content of the photopolymerization initiator (b) in the present invention is 0.1 to 10.0% by mass based on the total amount of the curable composition of the present invention from the standpoint of the curing capability of the resulting resin composition for stereolithography, and the like. The content thereof is more preferably 0.5% by mass or more, and further preferably 1.0% by mass or more. In the case where the content of the photopolymerization initiator (b) exceeds 10.0% by mass based on the curable composition of the present invention, there is a concern that the photopolymerization initiator is deposited from the curable composition in the case where the solubility thereof is low. The content of the photopolymerization initiator (b) is more preferably 7.5% by mass or less, and further preferably 5.5% by mass or less, based on the curable composition of the present invention.

[Polyfunctional Polymerizable Compound (c)]

The polyfunctional polymerizable compound (c) used in the present invention is a compound represented by the following general formula (I).

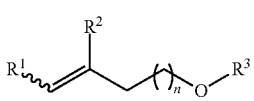

(I)

In the general formula (I), $R^1$ and $R^2$ each independently represent at least one kind selected from the group consisting of a hydrogen atom, an alkyl group having 1 to 6 carbon atoms, an alkenyl group having 2 to 6 carbon atoms, an aryl group, and an aralkyl group; $R^3$ represents at least one kind of a polymerizable functional group selected from the group consisting of a (meth)acryloyl group, a 4-vinylphenyl group, and an alkenyl group having 2 to 5 carbon atoms; and n represents an arbitrary integer of 0 to 5.

Examples of the alkyl group having 1 to 6 carbon atoms represented by $R^1$ and $R^2$ include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a n-hexyl group, a cyclopropyl group, a cyclobutyl group, a cyclopentyl group, a cyclohexyl group.

Examples of the alkenyl group having 2 to 6 carbon atoms represented by $R^1$ and $R^2$ include a vinyl group, an allyl group, a propenyl group, an isopropenyl group, a butenyl group, an isobutenyl group, a pentenyl group, a hexenyl group (such as a cis-3-hexenyl group), and a cyclohexenyl group.

The aryl group represented by $R^1$ and $R^2$ is preferably an aryl group having 6 to 18 carbon atoms, and examples thereof include a phenyl group, a tolyl group, a xylyl group, and a naphthyl group.

The aralkyl group represented by $R^1$ and $R^2$ is preferably an aralkyl group having 7 to 18 carbon atoms, and examples thereof include a benzyl group, a 2-phenylethyl group, a 2-naphthylethyl group, and a diphenylmethyl group.

In the general formula (I), the wave line between $R^1$ and the double bond connected thereto means that there is no limitation in kind of the geometric isomers derived from the double bond. Specifically, in the case where R' represents a group other than a hydrogen atom, $R^1$ may be in the cis position with respect to $R^2$ or may be in the trans position with respect thereto.

$R^1$ and $R^2$ each preferably represent at least one kind selected from the group consisting of a hydrogen atom, an alkyl group having 1 to 6 carbon atoms, and an alkenyl group having 2 to 6 carbon atoms, more preferably a hydrogen atom or an alkyl group having 1 to 6 carbon atoms, further preferably a hydrogen atom or an alkyl group having 1 to 4 carbon atoms, and particularly preferably a hydrogen atom or a methyl group. In particular, it is preferred that $R^1$ represents a hydrogen atom, and $R^2$ represents a hydrogen atom or a methyl group.

In the general formula (I), $R^3$ represents at least one kind selected from the group consisting of a (meth)acryloyl group, a 4-vinylphenyl group, and an alkenyl group having 2 to 5 carbon atoms.

Examples of the alkenyl group having 2 to 5 carbon atoms represented by $R^3$ include a vinyl group, an allyl group, a propenyl group, an isopropenyl group, a butenyl group, an isobutenyl group, and a pentenyl group.

Among these, $R^3$ preferably represents a (meth)acryloyl group or a 4-vinylphenyl group, and more preferably a (meth)acryloyl group, from the standpoint of the effective function as the polymerizable group and the significant achievement of the effects of the present invention.

In the general formula (I), n represents an arbitrary integer of 0 to 5. The value of n is preferably an arbitrary integer of 1 to 4, more preferably 1 or 2, and further preferably 1.

Specific examples of the polyfunctional polymerizable compound (c) include the following compounds.

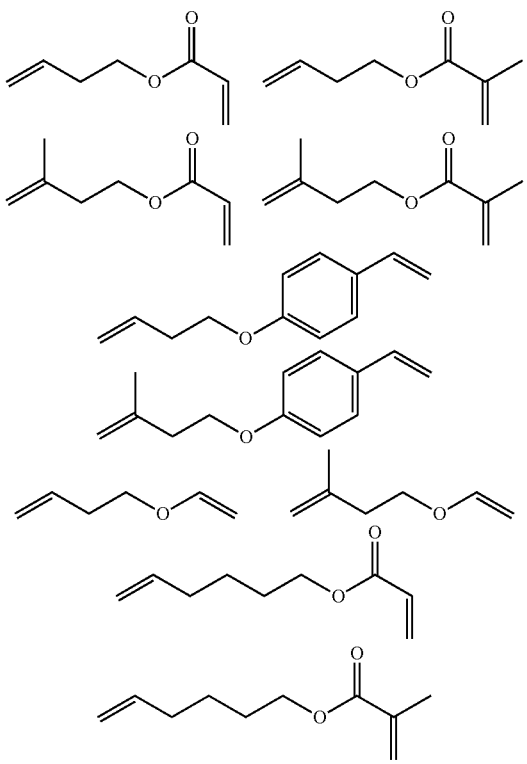

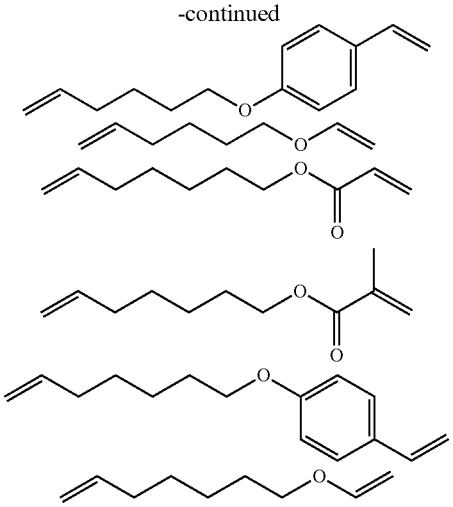

The polyfunctional polymerizable compound (c) is preferably a compound represented by the following general formula (II) from the standpoint of the availability of the raw material, and the like.

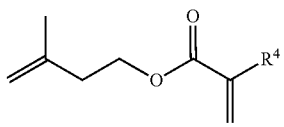

In the general formula (II), $R^4$ represents a hydrogen atom or a methyl group.

The production method of the polyfunctional polymerizable compound (c) is not particularly limited, and the compound can be produced by applying a known method alone or an appropriate combination of the known methods. For example, in the case where the polyfunctional polymerizable compound (c) represented by the following formula (A-1) is produced, the compound can be produced by reacting methyl methacrylate with 3-methyl-3-buten-1-ol, which is the corresponding alcohol, in the presence of an ester exchange reaction catalyst, such as a base.

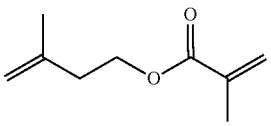

In the present invention, only one kind of the polyfunctional polymerizable compound (c) may be contained, and two or more kinds thereof may be contained.

The content of the polyfunctional polymerizable compound (c) in the composition of the present invention is 0.01% by mass or more, more preferably 0.1% by mass or more, and further preferably 0.5% by mass or more, from the standpoint of the curing capability of the resulting resin composition for stereolithography, and the like. The content thereof is 20.0% by mass or less, preferably 15.0% by mass or less, and further preferably 10.0% by mass or less, from the standpoint of the properties of the resulting cured article, and the like.

[Inorganic Particles (d)]

The curable composition of the present invention may contain inorganic particles (d). The inorganic particles (d) may be surface-treated in advance depending on necessity with a known surface treatment agent, such as an organic compound containing an acidic group; a fatty acid amide, such as a saturated fatty acid amide, an unsaturated fatty acid amide, a saturated fatty acid bisamide, and an unsaturated fatty acid bisamide; and an organic silicon compound, such as a silane coupling agent, for regulating the miscibility with the polymerizable monomer (a) and the polyfunctional polymerizable compound (c). The inorganic particles (d) are preferably surface-treated with an organic compound containing an acidic group for the enhancement of the chemical bonding capability among the polymerizable monomer (a), the polyfunctional polymerizable compound (c), and the inorganic particles (d), so as to enhance the mechanical strength of the cured article. Examples of the acidic group-containing organic compound include an organic compound having at least one group of an acidic group, such as a phosphoric acid group, a pyrophosphoric acid group, a thiophosphoric acid group, a phosphonic acid group, a sulfonic acid group, and a carboxylic acid group, and an organic compound having at least one phosphoric acid group is preferred. In the case where two or more kinds of the surface treatment agents are used, a surface treatment layer of a mixture of the two or more kinds of the surface treatment agents may be used, and a surface treatment layer having a multiple layer structure including plural surface treatment agent layers laminated.

Examples of the acidic group-containing organic compound having a phosphoric acid group include 2-ethylhexyl acid phosphate, stearyl acid phosphate, 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis(2-(meth)acryloyloxyethyl) hydrogen phosphate, bis(4-(meth)acryloyloxybutyl) hydrogen phosphate, bis(6-(meth)acryloyloxyhexyl) hydrogen phosphate, bis(8-(meth)acryloyloxyoctyl) hydrogen phosphate, bis(9-(meth)acryloyloxynonyl) hydrogen phosphate, bis(10-(meth)acryloyloxydecyl) hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, bis(2-(meth)acryloyloxy-(1-hydroxymethyl)ethyl) hydrogen phosphate, and acid chlorides, alkali metal salts, and ammonium salts of these compounds.

Examples of the acidic group-containing organic compound having such an acidic group as a pyrophosphoric acid group, a thiophosphoric acid group, a phosphonic acid group, a sulfonic acid group, and a carboxylic acid group include the compounds described in WO 2012/042911, which may be preferably used.

Examples of the saturated fatty acid amide include palmitic acid amide, stearic acid amide, and behenic acid amide. Examples of the unsaturated fatty acid amide include oleic acid amide and erucic acid amide. Examples of the saturated fatty acid bisamide include ethylene bispalmitic acid amide, ethylene bisstearic acid amide, and hexamethylene bisstearic acid amide. Examples of the unsaturated fatty acid bisamide include ethylene bisoleic acid amide, hexamethylene bisoleic acid amide, and N,N'-dioleylsebacic acid amide.

Examples of the organic silicon compound include a compound represented by $R^1{}_n SiX_{4-n}$. In the formula, $R^1$ represents a saturated or unsaturated hydrocarbon group having 1 to 12 carbon atoms, X represents an alkoxy group having 1 to 4 carbon atoms, a hydroxy group, a halogen atom, or a hydrogen atom, and n represents an integer of 0 to 3, provided that in the case where plural groups exist for each of $R^1$ and X, the groups may be the same as or different from each other.

Specific examples thereof include methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyltris(3-methoxyethoxy)silane, 3,3,3-trifluoropropyltrimethoxysilane, methyl-3,3,3-trifluoropropyldimethoxysilane, β-(3,4-ep oxycyclohexyl)ethyltrimethoxysilane, γ-glycidoxypropyltrimethoxysilane, γ-glycidoxypropylmethyldiethoxysilane, γ-glycidoxypropyltriethoxysilane, γ-methacryloyloxypropylmethyldimethoxysilane, γ-methacryloyloxypropylmethyldiethoxysilane, N-β-(aminoethyl)-γ-aminopropylmethyldimethoxysilane, N-β-(aminoethyl)-γ-aminopropyltrimethoxysilane, N-β-(aminoethyl)-γ-aminopropyltriethoxysilane, γ-aminopropyltrimethoxysilane, γ-aminopropyltriethoxysilane, N-phenyl-γ-aminopropyltrimethoxysilane, γ-mercaptopropyltrimethoxysilane, trimethylsilanol, methyltrichlorosilane, methyldichlorosilane, dimethyldichlorosilane, trimethylchlorosilane, phenyltrichlorosilane, diphenyldichlorosilane, vinyltrichlorosilane, trimethylbromosilane, diethylsilane, vinyltriacetoxysilane, an ω-(meth)acryloyloxyalkyltrimethoxysilane (number of carbon atoms between (meth)acryloyloxy group and silicon atom: 3 to 12, e.g., γ-methacryloyloxypropyltrimethoxysilane), and an ω-(meth)acryloyloxyalkyltriethoxysilane (number of carbon atoms between (meth)acryloyloxy group and silicon atom: 3 to 12, e.g., γ-methacryloyloxypropyltriethoxysilane).

Among these, a silane coupling agent having a functional group capable of being copolymerized with the polymerizable monomer (a) and the polyfunctional polymerizable compound (c), such as an ω-(meth)acryloyloxyalkyltrimethoxysilane (number of carbon atoms between (meth) acryloyloxy group and silicon atom: 3 to 12), an ω-(meth) acryloyloxyalkyltriethoxysilane (number of carbon atoms between (meth)acryloyloxy group and silicon atom: 3 to 12), vinyltrimethoxysilane, vinyltriethoxysilane, vinyltriacetoxysilane, and γ-glycidoxypropyltrimethoxysilane, is preferably used.

The method for the surface treatment may be a known method applied thereto without particular limitation, and examples thereof include a method of adding by spraying the surface treatment agent to the inorganic particles (d) under vigorous agitation, and a method of dispersing or dissolving the inorganic particles (d) and the surface treatment agent in an appropriate solvent, followed by removing the solvent.

The amount of the surface treatment agent used is not particularly limited, and for example, is preferably 0.1 to 50.0 parts by mass, more preferably 0.3 to 40.0 parts by mass, and further preferably 0.5 to 30.0 parts by mass, per 100.0 parts by mass of the inorganic particles (d).

The content of the inorganic particles (d) in the curable composition of the present invention is preferably 0.0 to 80.0% by mass, more preferably 1.0 to 60.0% by mass, and further preferably 3.0 to 40.0% by mass, based on the total amount of the curable composition, from the standpoint of the viscosity of the resulting curable composition and resin composition for stereolithography, and the modeling accuracy and the toughness of the cured article.

The curable composition of the present invention is not particularly limited, as far as the curable composition contains the polymerizable monomer (a), the photopolymerization initiator (b), and the polyfunctional polymerizable compound (c) described above in the prescribed amounts, may contain the inorganic particles (d) depending on necessity, and for example, may further contain an additional component other than these. The content of the additional component in the curable composition (i.e., the component other than the polymerizable monomer (a), the photopolymerization initiator (b), the polyfunctional polymerizable compound (c), and depending on necessity the inorganic particles (d)) may be less than 3% by mass, may be less than 2% by mass, and may be less than 1% by mass. The curable composition and the resin composition for stereolithography of the present invention may be produced according to a known method.

The curable composition of the present invention may contain an organic ultraviolet ray absorbent for the further enhancement of the modeling accuracy.

Examples of the organic ultraviolet ray absorbent include a benzotriazole based compound, a benzophenone based compound, and a thiophene based compound. The benzotriazole based compound is preferably a compound having a hydroxy group bonded to the 2-position of the aromatic ring bonded to the nitrogen atom of the triazole structure, and, from the standpoint of more excellent modeling accuracy, more preferably a compound having a hydroxy group bonded to the 2-position of the aromatic ring bonded to the nitrogen atom of the triazole structure, and an alkyl group having 1 to 10 carbon atoms bonded to the 3-position and/or the 5-position of the aromatic ring. Examples of the benzotriazole based compound include 2-(2-hydroxy-5-methylphenyl)benzotriazole ("TINUVIN P"), 2-(2-hydroxy-5-tert-octylphenyl)benzotriazole ("TINUVIN 329"), 2-(2'-hydroxy-3',5'-di-tert-butylphenyl)benzotriazole, 2-(2'-hydroxy-5'-tert-butylphenyl)benzotriazole, 2-(2'-hydroxy-3'-tert-butyl-5'-methylphenyl)benzotriazole, 2-(2'-hydroxy-3',5'-di-tert-amylphenyl)benzotriazole, 2-(2'-hydroxy-3'-tert-butyl-5'-methylphenyl)benzotriazole, 2-(2'-hydroxy-3'-tert-butyl-5'-methylphenyl)-5-chlorobenzotriazole, and 2-(2'-hydroxy-3',5'-di-tert-butylphenyl)-5-chlorobenzotriazole. Examples of the benzophenone based compound include 2,4-dihydroxybenzophenone, 2-hydroxy-4-methoxybenzophenone, 2-hydroxy-4-n-octoxybenzophenone, 2-hydroxy-4-(dodecyloxy)benzophenone, 2-hydroxy-4-(octadecyloxy)benzophenone, 2,2'-dihydroxy-4-methoxybenzophenone, and 2,2'-dihydroxy-4,4'-dimethoxybenzophenone. Examples of the thiophene based compound include 2,5-bis(5-t-butyl-2-benzoxazolyl)thiophene. Among these, a benzotriazole based compound is preferred from the standpoint of the achievement of the good modeling accuracy.

The organic ultraviolet ray absorbent may be used alone or as a combination of two or more kinds thereof. The content of the organic ultraviolet ray absorbent is preferably in a range of 0.001 to 10.0% by mass, more preferably in a range of 0.01 to 5.0% by mass, and further preferably 0.1 to 2.5% by mass, based on the total amount of the curable composition.

The curable composition of the present invention may contain a polymerization accelerator in a range that does not impair the effects of the present invention, for the purpose of enhancing the photocuring capability. Examples of the polymerization accelerator include ethyl 4-(N,N-dimethylamino)benzoate, methyl 4-(N,N-dimethylamino)benzoate, n-butoxyethyl 4-(N,N-dimethylamino)benzoate, 2-(methacryloyloxy)ethyl 4-N,N-dimethylaminobenzoate, 4-(N,N-dimethylamino)benzophenone, and butyl 4-(N,N-dimethylamino)benzoate. Among these, at least one selected from the group consisting of ethyl 4-(N,N-dimethylamino)benzoate, n-butoxyethyl 4-(N,N-dimethylamino)benzoate, and 4-(N,N-dimethylamino)benzophenone is preferably used from the standpoint that excellent curing capability is imparted to the resin composition for stereolithography.

The curable composition of the present invention may contain a known stabilizer for the purpose of suppressing the deterioration and regulating the photocuring capability. Examples of the stabilizer include a polymerization inhibitor and an antioxidant.

Examples of the polymerization inhibitor include hydroquinone, hydroquinone monomethyl ether, dibutylhydroquinone, dibutylhydroquinone monomethyl ether, t-butylcatechol, 2-t-butyl-4,6-dimethylphenol, 2,6-di-t-butylphenol, and 3,5-di-t-butyl-4-hydroxytoluene. The content of the polymerization inhibitor is preferably 0.001 to 2.0 parts by mass per 100.0 parts by mass in total of the polymerizable monomer (a).

The resin composition for stereolithography of the present invention may contain a known additive for the purpose of regulating the color tone and the paste property. Examples of the additive include a pigment, a dye, an organic solvent, and a thickener.

The resin composition for stereolithography of the present invention not only is readily modeled with low viscosity, but also has good modeling accuracy, and a stereolithography resin cured article obtained by curing the resin composition for stereolithography is excellent in toughness and water resistance. Accordingly, the resin composition for stereolithography of the present invention can be applied to such purposes that can exploit these advantages, and for example, can be applied to various stereoscopic modeled articles produced by the optical stereoscopic modeling method. Among these, the resin composition for stereolithography can be preferably applied to a dental material, a dental mouthpiece, a denture base material, a medical material, and a sleep apnea syndrome treatment device, and is particularly optimum as a dental mouthpiece and a denture base material.

As another embodiment, the present invention relates to a method for producing a stereoscopic modeled article by the suspension optical stereoscopic modeling method using any of the resin compositions for stereolithography described above.

In the optical stereoscopic modeling performed with the resin composition for stereolithography of the present invention, any of the known suspension optical stereoscopic modeling methods and the known apparatuses therefor may be used. Among these, in the present invention, the method and apparatus using an activation energy ray as light energy for curing the resin are preferably used. The "activation energy ray" referred in the present invention means an energy ray capable of curing the photocurable resin composition, such as an ultraviolet ray, an electron beam, an X-ray, a radioactive ray, and a high frequency wave. For example, the activation energy ray may be an ultraviolet ray having a wavelength of 300 to 400 nm. Examples of the light source of the activation energy ray include a laser, such as an Ar laser and a He-Cd laser, and an illumination, such as a halogen lamp, a xenon lamp, a metal halide lamp, an LED, a mercury lamp, and a fluorescent lamp, and a laser is particularly preferred. In the case where a laser is used as the light source, the modeling time can be shortened by increasing the energy level, and furthermore a stereoscopic modeled article having high modeling accuracy can be obtained by the good light focusing capability of laser light.

In the optical stereoscopic modeling performed with the resin composition for stereolithography of the present invention, any of the known methods and the known stereolithography apparatuses may be used without particular limitation, as described above, and representative examples of the optical stereoscopic modeling method that is preferably used in the present invention include a method of providing a target stereoscopic modeled article by repeating an operation including a step of providing a cured layer by irradiating the composition for optical stereoscopic modeling with an activation energy ray selectively to provide the cured layer having a target pattern, and then a step of suspending the cured layer, supplying the uncured composition for optical stereoscopic modeling in the form of liquid, and irradiating the composition similarly with an activation energy ray, so as to provide a new cured layer continuous to the cured layer. The stereoscopic modeled article thus obtained may be used immediately, or in some cases, may be used after enhancing the mechanical characteristics or the dimensional stability thereof by performing post-curing by light irradiation or post-curing by heating.

EXAMPLES

The present invention will be then described more specifically with reference to examples, but the present invention is not limited to the examples, and many changes may be made therein within the scope of the technical concept of the present invention by a skilled person in this field of art.

The evaluation method used in Synthesis Examples and Examples is described below.

Measurement of Weight Average Molecular Weight by GPC

The measurement was performed with columns: TSK-gel SUPER HZM-H (trade name, produced by Tosoh Corporation, 4.6 mm×150 mm)×2 and TSK-gel SUPER HZ2000 (produced by Tosoh Corporation, 4.6 mm×150 mm)×1, connected in series, eluent: tetrahydrofuran, and calibration curve: polystyrene standard.

The components used in the resin compositions for stereolithography according to Examples and Comparative Examples are shown below along with the abbreviations thereof.

[Polymerizable Monomer (a)-1]

D26E: 2,2-bis(4-methacryloyloxypolyethoxyphenyl)propane (produced by Shin-Nakamura Chemical Co., Ltd.)

[Polymerizable Monomer (a)-1α]

A polymerizable monomers (a)-1α-1 and (a)-1α-2 produced in Synthesis Examples 1 and 2 described later were used.

[Polymerizable Monomer (a)-2]

EPPA: ethoxylated, o-phenylphenol acrylate (produced by Shin-Nakamura Chemical Co., Ltd.)

POBA: m-phenoxybenzyl methacrylate (produced by Kyoeisha Chemical Co., Ltd.)

ACMO: N-acryloylmorpholine (produced by KJ Chemicals Corporation)

[Photopolymerization Initiator (b)]

TPO: 2,4,6-trimethylbenzoyldiphenylphosphine oxide

BAPO: bis(2,4,6-trimethylbenzoyl)phenylphosphine oxide

[Polyfunctional Polymerizable Compound (c)]

IPEMA: isoprenyl methacrylate represented by the following formula (C-1) (produced by Kuraray Co., Ltd.)

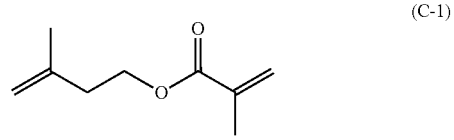

[Inorganic Particles (d)]

Ar130: Aerosil 130

[Polymerization Inhibitor]

BHT: 3,5-di-t-butyl-4-hydroxytoluene

Synthesis Example 1

[Production of Polymerizable Monomer (a)-1α-1]

(1) 250 g of isophorone diisocyanate and 0.15 g of di-n-butyltin dilaurate were added to a four-neck flask having a capacity of 5 L equipped with an agitator, a temperature controller, a thermometer, and a condenser, and heated to 70° C. under agitation.

(2) Separately, 2,500 g of a polyester polyol ("KURARAY POLYOL (trade name) P-2050", produced by Kuraray Co., Ltd., a polyol formed of sebacic acid and 3-methylpentanediol, weight average molecular weight: 2,000) was added to a dropping funnel having a side tube, and the liquid in the dropping funnel was added dropwise to the flask in the item (1) above. The dropwise addition was performed at a constant rate over 4 hours while retaining the inner temperature of the flask to 65 to 75° C. under agitation of the solution in the flask in the item (1) above. After completing the dropwise addition, the reaction was performed at the same temperature for 2 hours under agitation.

(3) Subsequently, a liquid obtained by dissolving uniformly 150 g of 2-hydroxyethyl acrylate and 0.4 g of hydroquinone monomethyl ether was added to another dropping funnel and added dropwise at a constant rate to the flask having an inner temperature retained to 55 to 65° C. over 2 hours, and then the reaction was performed for 4 hours while retaining the temperature of the solution in the flask to 70 to 80° C., so as to provide a polymerizable monomer (a)-1α-1. The weight average molecular weight of the polymerizable monomer (a)-1α-1 by the GPC analysis was 2,600 g/mol.

Synthesis Example 2

[Production of Polymerizable Monomer (a)-1α-2]

(1) 250 g of isophorone diisocyanate and 0.15 g of di-n-butyltin dilaurate were added to a four-neck flask having a capacity of 5 L equipped with an agitator, a temperature controller, a thermometer, and a condenser, and heated to 70° C. under agitation.

(2) Separately, 2,500 g of a polyester polyol ("KURARAY POLYOL (trade name) P-2030", produced by Kuraray Co., Ltd., a polyol formed of isophthalic acid and 3-methylpentanediol, weight average molecular weight: 2,000 g/mol) was added to a dropping funnel having a side tube, and the liquid in the dropping funnel was added dropwise to the flask in the item (1) above. The dropwise addition was performed at a constant rate over 4 hours while retaining the inner temperature of the flask to 65 to 75° C. under agitation of the solution in the flask in the item (1) above. After completing the dropwise addition, the reaction was performed at the same temperature for 2 hours under agitation.

(3) Subsequently, a liquid obtained by dissolving uniformly 150 g of 2-hydroxyethyl acrylate and 0.4 g of hydroquinone monomethyl ether was added to another dropping funnel and added dropwise at a constant rate to the flask having an inner temperature retained to 55 to 65° C. over 2 hours, and then the reaction was performed for 4 hours while retaining the temperature of the solution in the flask to 70 to 80° C., so as to provide a polymerizable monomer (a)-1α-2. The weight average molecular weight of the polymerizable monomer (a)-1α-2 by the GPC analysis was 2,700 g/mol.

Examples 1 to 9 and Comparative Examples 1 to 4

The components in amounts shown in Tables 1 and 2 were mixed at ordinary temperature (20° C.±15° C., JIS Z8703: 1983), so as to provide pastes as resin compositions for stereolithography according to Examples 1 to 9 and Comparative Examples 1 to 4.

<Modeling Capability>

The resin compositions for stereolithography according to Examples and Comparative Examples each were modeled to provide a test piece of 2.0 mm in thickness×20.0 mm in width×and 60.0 mm in length, with a stereolithography machine (Digitalwax (trade name) 020D, produced by DWS Systems Inc.). The case where a sheet having the prescribed dimension could be modeled with an error of 0.5 mm or less for each edge was designated as "A", i.e., the modeling was possible, and the case where a stereoscopic modeled article was not obtained was designated as "X", i.e., the modeling was impossible. The test pieces thus modeled each were subjected to the evaluation shown below.

<Toughness (Hand Flex Test)>

For each of cured articles of the resin compositions for stereolithography according to Examples and Comparative Examples, the aforementioned test piece (length: 60.0 mm, width: 20.0 mm, thickness (height): 2.0 mm) was evaluated by a hand flex test. Specifically, the test piece was folded in half and then opened by hand, and the operation was repeated. In this test, the preferred was no breakage, the case where the test piece was not broken after repetition of 10 times was designated as good toughness "A", the case where the test piece was broken after repetition of 3 to 10 times was designated as medium toughness "B", and the case where the test piece was broken after repetition of less than 3 times was designated as poor toughness "C".

<A Hardness (Flexibility Test)>

For each of cured articles of the resin compositions for stereolithography according to Examples and Comparative Examples, two sheets of the aforementioned test piece were overlapped to a thickness of 4 mm, and the hardness (A hardness) at 23° C. of the cured article was measured with a type A durometer according to JIS K7215:1986, and designated as the index of flexibility. In the case where the A hardness at 23° C. is 70 to 90 in this test, the cured article has flexibility suitable for a dental mouthpiece and a denture base material.

<Water Resistance>

For each of cured articles of the resin compositions for stereolithography according to Examples and Comparative Examples, the test piece was immersed in water at 37° C. for 24 hours, and then measured for the A hardness in the same manner as above. The case where the decrease of the hardness after the immersion in water at 37° C. for 24 hours with respect to the initial hardness is 3 points or less is excellent in water resistance.

TABLE 1

|  |  |  | Example | | | | | | | | | |
|---|---|---|---|---|---|---|---|---|---|---|---|---|
|  |  |  | 1 | 2 | 3 | 4 | 5 | 6 | 7 | 8 | 9 |
| Formulation (part by mass) | (a)-1 | D26E | 10.0 | 14.0 | 5.0 | 10.0 | 10.0 | 10.0 | 10.0 |  | 10.0 |
|  |  | (a)-1α-1 | 40.0 | 40.0 | 40.0 | 20.0 | 55.0 |  |  |  | 20.0 |
|  |  | (a)-1α-2 |  |  |  |  |  | 40.0 | 40.0 | 45.0 |  |
|  | (a)-2 | EPPA | 45.0 | 45.0 | 45.0 | 60.0 | 30.0 | 45.0 |  |  | 60.0 |
|  |  | POBA |  |  |  |  |  |  | 45.0 | 40.0 |  |
|  |  | ACMO |  |  |  | 5.0 |  |  |  | 5.0 | 5.0 |
|  | (b) | TPO | 5.0 | 5.0 | 5.0 | 5.0 | 3.0 | 5.0 | 5.0 | 5.0 | 5.0 |
|  |  | BAPO |  |  |  |  | 0.5 |  |  |  |  |
|  | (c) | IPEMA | 5.0 | 1.0 | 10.0 | 5.0 | 5.0 | 5.0 | 5.0 | 10.0 | 5.0 |
|  | (d) | Ar380 |  |  |  |  |  |  |  |  | 5.0 |
|  |  | BHT | 1.0 | 1.0 | 1.0 | 1.0 | 1.0 | 1.0 | 1.0 | 1.0 | 1.0 |
| Content of (a) (% by mass) |  |  | 89.6 | 93.4 | 84.9 | 89.2 | 91.3 | 89.6 | 89.6 | 84.9 | 85.6 |
| Content of (b) (% by mass) |  |  | 4.7 | 4.7 | 4.7 | 5.2 | 2.9 | 4.7 | 4.7 | 4.7 | 4.5 |
| Content of (c) (% by mass) |  |  | 4.7 | 0.9 | 9.4 | 4.7 | 4.8 | 4.7 | 4.7 | 9.4 | 4.5 |
| Evaluation | Modeling capability |  | A | A | A | A | A | A | A | A | A |
|  | Toughness (hand flex test) |  | A | A | A | A | A | A | A | A | A |
|  | A hardness (flexibility test) |  | 80 | 84 | 78 | 79 | 82 | 88 | 86 | 87 | 84 |
|  | Water resistance (hardness after immersion) |  | 80 | 83 | 79 | 77 | 81 | 88 | 85 | 84 | 82 |

TABLE 2

|  |  |  | Comparative Example | | | |
|---|---|---|---|---|---|---|
|  |  |  | 1 | 2 | 3 | 4 |
| Formulation (part by mass) | (a)-1 | D26E | 15.0 | 15.0 | 15.0 | 15.0 |
|  |  | (a)-1α-1 | 40.0 |  | 55.0 | 20.0 |
|  |  | (a)-1α-2 |  | 40.0 |  |  |
|  | (a)-2 | EPPA | 45.0 | 45.0 | 30.0 | 60.0 |
|  |  | ACMO |  |  |  | 5.0 |
|  | (b) | TPO | 5.0 | 5.0 | 5.0 | 5.0 |
|  | (c) | IPEMA |  |  |  |  |
|  | (d) | Ar130 |  |  |  | 10.0 |
|  |  | BHT | 1.0 | 1.0 | 1.0 | 1.0 |
| Content of (a) (% by mass) |  |  | 94.3 | 94.3 | 94.3 | 86.2 |

TABLE 2-continued

|  |  | Comparative Example | | | |
|---|---|---|---|---|---|
|  |  | 1 | 2 | 3 | 4 |
|  | Content of (b) (% by mass) | 4.7 | 4.7 | 4.7 | 4.3 |
|  | Content of (c) (% by mass) | 0.0 | 0.0 | 0.0 | 0.0 |
| Evaluation | Modeling capability | A | A | X | X |
|  | Toughness (hand flex test) | C | C | — | — |
|  | A hardness (flexibility test) | 82 | 94 | — | — |
|  | Water resistance (hardness after immersion) | 75 | 91 | — | — |

As shown in Tables 1 and 2, the resin compositions for stereolithography in Examples 1 to 9 were excellent in modeling capability. Furthermore, the cured articles thereof were excellent in toughness and water resistance. In particular, the toughness and the water resistance of the cured articles of the resin compositions for stereolithography according to Examples 1 to 9 were excellent as compared to the cured articles of the resin compositions according to Comparative Examples 1 and 2 that did not contain the polyfunctional polymerizable compound (c) of the present invention. The modeling capability of the resin compositions for stereolithography according to Examples 1 to 9 was excellent as compared to the resin compositions according to Comparative Examples 3 and 4. In Comparative Examples 3 and 4, modeling was difficult due to the increase in viscosity.

INDUSTRIAL APPLICABILITY

The resin composition for stereolithography of the present invention is readily modeled with low viscosity in modeling by stereolithography and is excellent in modeling accuracy, and therefore is favorable as a dental material, particularly a dental modeling material.

The invention claimed is:

1. A curable composition comprising
79.0 to 99.0% by mass of a polymerizable monomer (a), wherein the polymerizable monomer (a) contains a polymerizable monomer (a)-1 containing plural polymerizable groups, wherein the polymerizable monomer (a)-1 contains a urethanated (meth)acrylic compound (a)-1α having in one molecule thereof at least one structure selected from the group consisting of a 3-methylpentanediol-derived constituent unit,
0.1 to 10.0% by mass of a photopolymerization initiator (b), and
0.01 to 20.0% by mass of a compound represented by the following general formula (I) as a polyfunctional polymerizable compound (c):

$$R^1\underset{}{\diagdown}\underset{R^2}{\diagup}(\phantom{x})_n O - R^3 \tag{I}$$

wherein $R^1$ and $R^2$ each independently represent at least one kind selected from the group consisting of a hydrogen atom, an alkyl group having 1 to 6 carbon atoms, an alkenyl group having 2 to 6 carbon atoms, an aryl group, and an aralkyl group; $R^3$ represents at least one kind of a polymerizable functional group selected from the group consisting of a (meth)acryloyl group, a 4-vinylphenyl group, and an alkenyl group having 2 to 5 carbon atoms; and n represents an arbitrary integer of 0 to 5.

2. A resin composition for stereolithography comprising the curable composition according to claim 1.

3. The resin composition for stereolithography according to claim 2, wherein in the general formula (I), $R^1$ represents a hydrogen atom.

4. The resin composition for stereolithography according to claim 2, wherein in the general formula (I), $R^3$ represents a (meth)acryloyl group.

5. The resin composition for stereolithography according to claim 2, wherein the polyfunctional polymerizable compound (c) is represented by the following general formula (II):

$$\tag{II}$$

wherein $R^4$ represents a hydrogen atom or a methyl group.

6. The resin composition for stereolithography according to claim 2, wherein the polymerizable monomer (a) contains a monofunctional polymerizable monomer (a)-2.

7. The resin composition for stereolithography according to claim 6, wherein the monofunctional polymerizable monomer (a)-2 contains a ring structure.

8. The resin composition for stereolithography according to claim 2, wherein the resin composition further comprises inorganic particles (d).

9. A stereolithography resin cured article comprising a cured article of the resin composition for stereolithography according to claim 2.

10. A dental material comprising a cured article of the resin composition for stereolithography according to claim 2.

11. A dental mouthpiece comprising a cured article of the resin composition for stereolithography according to claim 2.

12. A denture base material comprising a cured article of the resin composition for stereolithography according to claim 2.

13. A medical material comprising a cured article of the resin composition for stereolithography according to claim 2.

14. A sleep apnea syndrome treatment device comprising a cured article of the resin composition for stereolithography according to claim 2.

15. A method for producing a stereoscopic modeled article by an optical stereoscopic modeling method, comprising using the resin composition for stereolithography according to claim 2.

16. The curable composition according to claim 1, wherein said curable composition comprises 0.01 to 15.0% by mass of said compound represented by the general formula (I) as a polyfunctional polymerizable compound (c).

17. A curable composition comprising
79.0 to 99.0% by mass of a polymerizable monomer (a), wherein the polymerizable monomer (a) contains a polymerizable monomer (a)-1 containing plural polymerizable groups, wherein the polymerizable monomer (a)-1 contains a urethanated (meth)acrylic compound (a)-1α having in one molecule thereof at least one structure selected from the group consisting of a semi-aromatic polyesters, 0.1 to 10.0% by mass of a photopolymerization initiator (b), and 0.01 to 20.0% by mass of a compound represented by the following general formula (I) as a polyfunctional polymerizable compound (c):

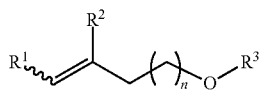

(I)

wherein $R^1$ and $R^2$ each independently represent at least one kind selected from the group consisting of a hydrogen atom, an alkyl group having 1 to 6 carbon atoms, an alkenyl group having 2 to 6 carbon atoms, an aryl group, and an aralkyl group; $R^3$ represents at least one kind of a polymerizable functional group selected from the group consisting of a (meth)acryloyl group, a 4-vinylphenyl group, and an alkenyl group having 2 to 5 carbon atoms; and n represents an arbitrary integer of 0 to 5.

18. A curable composition comprising 79.0 to 99.0% by mass of a polymerizable monomer (a), wherein the polymerizable monomer (a) contains a polymerizable monomer (a)-1 containing plural polymerizable groups, wherein the polymerizable monomer (a)-1 contains a urethanated (meth)acrylic compound (a)-1α having in one molecule thereof at least semi-aromatic polyester and a 3-methylpentanediol-derived constituent unit, 0.1 to 10.0% by mass of a photopolymerization initiator (b), and 0.01 to 20.0% by mass of a compound represented by the following general formula (I) as a polyfunctional polymerizable compound (c):

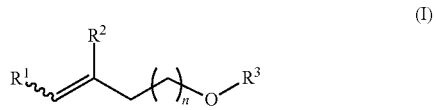

(I)

wherein $R^1$ and $R^2$ each independently represent at least one kind selected from the group consisting of a hydrogen atom, an alkyl group having 1 to 6 carbon atoms, an alkenyl group having 2 to 6 carbon atoms, an aryl group, and an aralkyl group; $R^3$ represents at least one kind of a polymerizable functional group selected from the group consisting of a (meth)acryloyl group, a 4-vinylphenyl group, and an alkenyl group having 2 to 5 carbon atoms; and n represents an arbitrary integer of 0 to 5.

* * * * *